US00PP25864P3

(12) United States Plant Patent
Clark

(10) Patent No.: US PP25,864 P3
(45) Date of Patent: Sep. 8, 2015

(54) BLACKBERRY PLANT NAMED 'A-2312'

(50) Latin Name: ***Rubus* subgenus *Rubus* Watson**
Varietal Denomination: A-2312

(71) Applicant: The Board of Trustees of the University of Arkansas, Little Rock, AR (US)

(72) Inventor: John Reuben Clark, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 330 days.

(21) Appl. No.: 13/573,628

(22) Filed: Sep. 27, 2012

(65) Prior Publication Data

US 2014/0090122 P1 Mar. 27, 2014

(51) Int. Cl.
*A01H 5/08* (2006.01)

(52) U.S. Cl.
USPC ..... Plt./203
CPC ..... *A01H 5/0887* (2013.01)

(58) Field of Classification Search
USPC ..... Plt./203
CPC ..... A01H 5/0887; A01H 5/08
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,865 | P2 | 5/2001 | Clark et al. |
| PP14,935 | P2 | 6/2004 | Clark |
| PP15,788 | P2 | 6/2005 | Clark |
| PP16,989 | P3 | 8/2006 | Clark et al. |
| PP17,162 | P3 | 10/2006 | Clark et al. |
| PP17,983 | P2 | 9/2007 | Cabrera Avalos |
| PP20,891 | P3 | 3/2010 | Clark |
| PP22,449 | P3 | 1/2012 | Clark |

OTHER PUBLICATIONS

Clark, J.R., et al., "'APF-45' primocane-fruiting blackberry." Hort. Science (2011) 46(4):670-673.
Ruple, A. et al., "An evaluation of fertility in Arkansas primocane-fruiting blackberries," (2010) Hort. Science 45:1-6 Office Action for U.S. Appl. No. 13/374,444 dated Jun. 6, 2013 (12 pages).
Office Action for U.S. Appl. No. 13/374,444 dated Jun. 6, 2013 (12 pages).
Press Release: "Pure Fresh marketing exclusive new Stella blackberry variety," The Produce News (Feb. 14, 2012).

*Primary Examiner* — Kent L Bell
(74) *Attorney, Agent, or Firm* — Andrus Intellectual Property Law, LLP

(57) ABSTRACT

Description and specifications of a new and distinct blackberry cultivar named 'A-2312' which originated from seed produced by a hand pollinated cross of Ark. Selection APF-1 (non-patented, unreleased genotype)×A-2002 (non-patented, unreleased genotype) is provided. This new blackberry cultivar can be distinguished by its firm, large, sweet fruit with excellent postharvest handling potential, attractive fruit appearance, very good flavor, excellent plant health, potential reduced chilling requirement compared to other cultivars, and high yields.

4 Drawing Sheets

Latin name: *Rubus* subgenus *Rubus* Watson.

BACKGROUND

The new cultivar of blackberry called 'A-2312' is described herein. The new cultivar originated from a hand-pollinated cross of Ark. Selection APF-1×A-2002 made in 2000. The seeds resulting from this controlled hybridization were germinated in a greenhouse in the spring of 2001 and planted in a field near Clarksville, Ark. (West-Central Arkansas). The seedlings fruited in the summer of 2002 and one seedling, designated 'A-2312', was selected for its firm, large, sweet fruit with excellent postharvest handling potential, attractive fruit appearance, very good flavor, excellent plant health, potential reduced chilling requirement compared to other cultivars, and high yields.

SUMMARY OF THE INVENTION

The new and distinct cultivar of blackberry originated from a hand-pollinated cross of Ark. Selection APF-1 (non-patented, unreleased genotype; female)×A-2002 (non-patented, unreleased genotype; male) made in 2000 and located near Clarksville, Ark. (West-Central Arkansas). The botanical designation of the new cultivar of blackberry is *Rubus* subgenus *Rubus* Watson.

The seeds resulting from this controlled hybridization were germinated in a greenhouse in the spring of 2001 and planted in a field near Clarksville, Ark. The seedlings fruited in the summer of 2002 on floricanes and one seedling, designated 'A-2312', was selected for its firm, large, sweet fruit with excellent postharvest handling potential, attractive fruit appearance, very good flavor, excellent plant health, potential reduced chilling requirement compared to other cultivars, and high yields.

During 2002, the original plant selection was propagated asexually from root cuttings at the above-noted location, and a test row of 10 plants was established. Subsequently, larger test plantings have been established with asexually multiplied plants at two locations in Arkansas. Additionally, the cultivar has been tested at test plots near Lincolnton, N.C., Watsonville, Calif. and in Guatemala with propagation from root cuttings from the Clarksville, Ark. test plot.

The new cultivar has been asexually reproduced annually since 2002 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

Test plantings over a wide geographic area have shown this new cultivar to be adapted to differing soil and climatic conditions. In testing in Guatemala, the reduced chilling requirement was confirmed due to good performance in this reduced-chilling environment.

BRIEF DESCRIPTION OF THE PHOTOGRAPHS

The accompanying photographs show typical specimens of the new variety in color as nearly true as it is reasonably possible to make in a color illustration of this character.

DETAILED DESCRIPTION OF THE NEW CULTIVAR 'A-2312'

Figure 1:
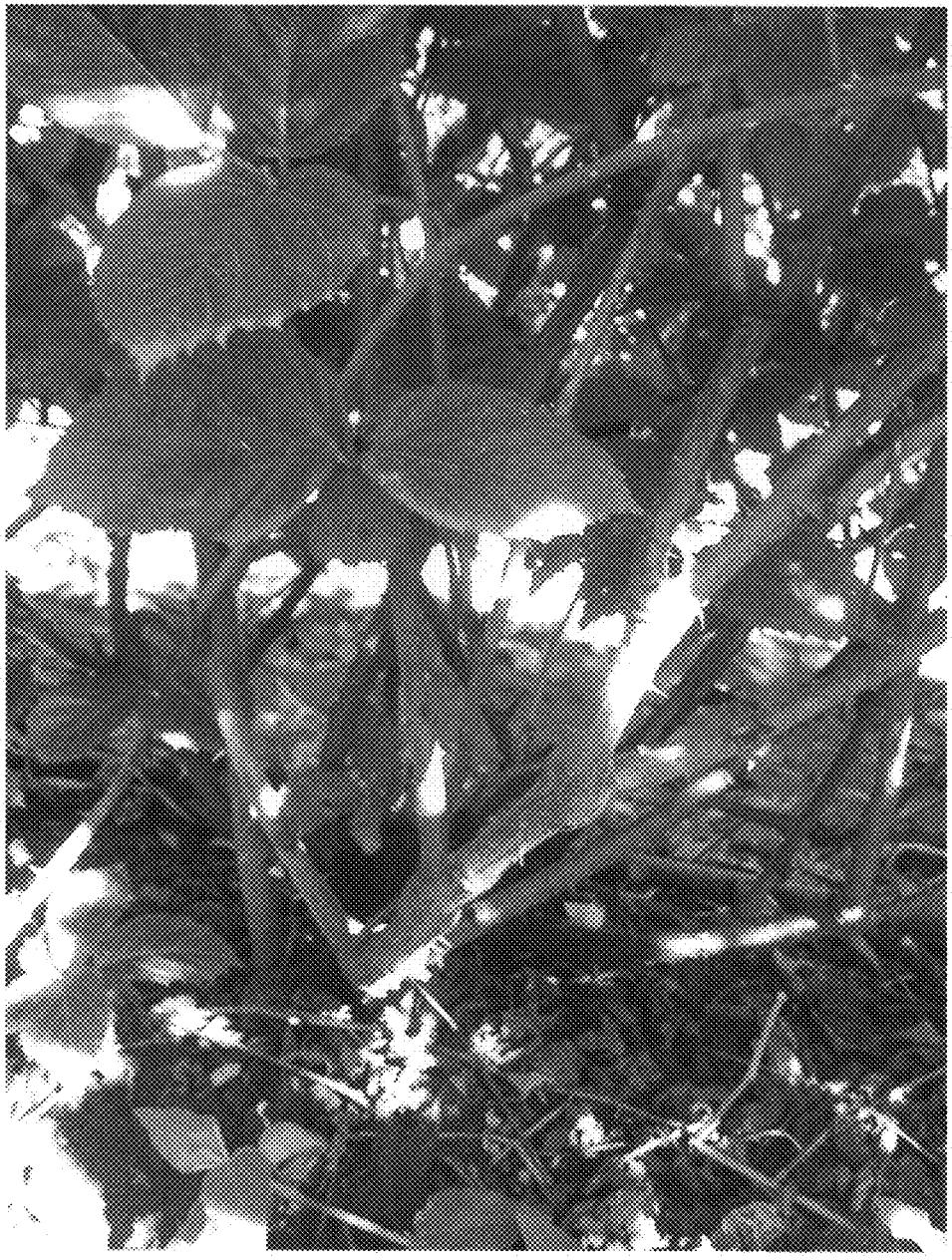
FIG. 1 is a photograph of primocane and floricane canes of 'A-2312'.
Figure 2:
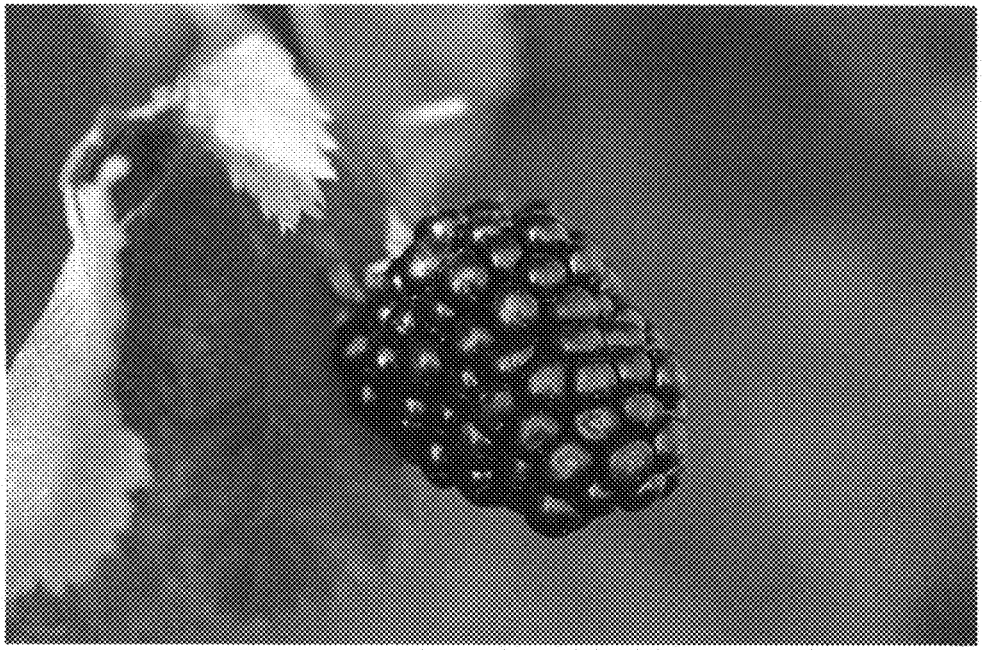
FIG. 2 is a photograph of ripe 'A-2312' fruit.
Figure 3:
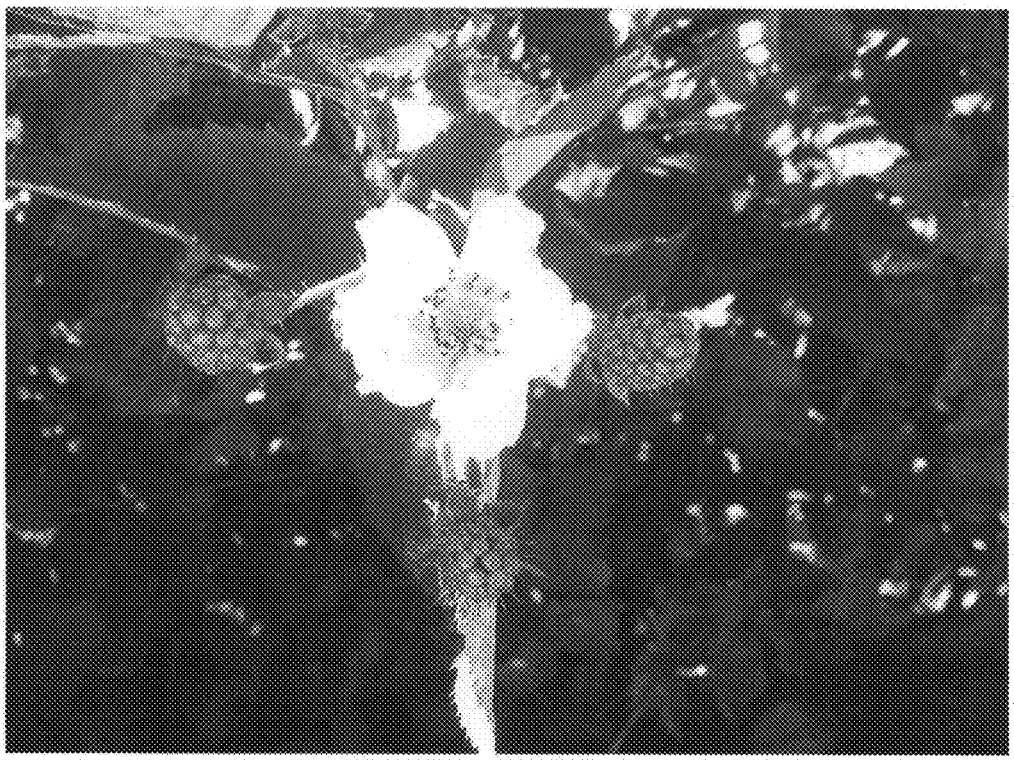
FIG. 3 is a photograph of the flower and immature fruit of 'A-2312'.
Figure 4:
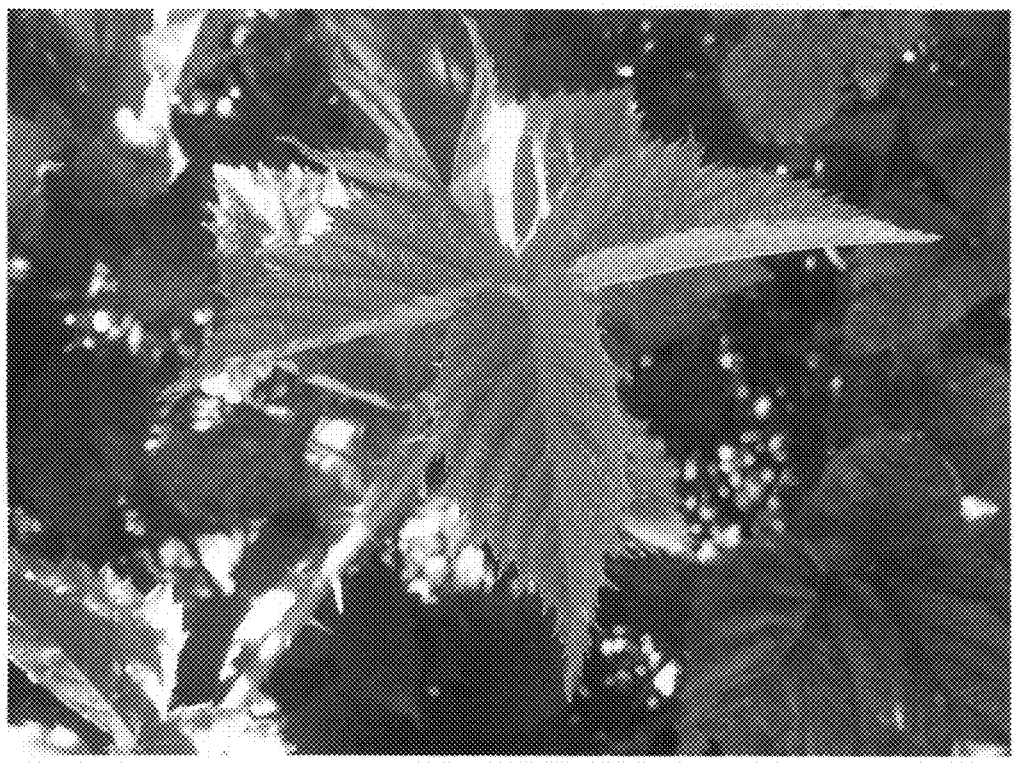
FIG. 4 is a photograph showing the adaxial side of a primocane leaf.

Plants and fruit of this new cultivar differ phenotypically from its parents. The new cultivar is more productive and has larger fruit and reduced chilling requirement compared to both parents. The new cultivar has sweeter fruit that has much better flavor and postharvest handling potential than either of the parent blackberries. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit-loads. The plants are thorny. Plants and fruit are moderately resistant to anthracnose [*Elsinoe veneta* (Burkh.) Jenkins], but plants are susceptible to orange rust [*Gymnoconia nitens* (Schwein.) F. Kern and H. W. Thurston.]. No screening has been done for resistance to double blossom/rosette [*Cercosporella rubi* (Wint.) Plakidas]

The floricane bloom period of the new cultivar begins on March 31 (10%) and average bloom lasts 12 days.

Floricane fruit of the new cultivar begins ripening on June 9, 3 days later than 'Natchez' (U.S. Plant Pat. No. 20,891). The average floricane fruiting period is 30-35 days.

Fruit yields of the new cultivar are on average 4.4 kg (9.7 lb/plant), comparable to that of 'Natchez', in West-Central Arkansas.

The fruit is elongated conical to blocky, bright glossy black in color, and very attractive. The floricane fruit is large (7-10 g) and 1.0 g larger than 'Natchez'. Floricane fruit size of the new cultivar is maintained well throughout the entire harvest season. The new cultivar exhibits excellent fruit fertility with full drupelet set. The fruit is firm at maturity, comparable to that of 'Natchez'. Storage potential of fresh fruit of the new cultivar is comparable to that of 'Ouachita' (U.S. Plant Pat. No. 17,162) and 'Natchez' and exceeds that of 'Prime-Jan' (U.S. Plant Pat. No. 15,788) cultivars.

The fresh fruit rates very good in flavor, comparable to 'Ouachita' and 'Natchez' cultivars. The flavor is very sweet and mildly acidic, with a distinct blackberry aroma. The soluble solids concentration averages 11.9% on shiny black fruit, higher than 'Natchez' (9.5%) and 'Ouachita' (10.4%).

Floricane fruit and flower clusters are medium-large, cymose, and are mostly borne on the periphery of the plant canopy, providing easy access to harvest. Flower fertility is high and clusters are well filled.

The following is a detailed description of the botanical and pomological characteristics of the subject blackberry. Color data are presented in The Royal Horticultural Society Colour Chart (1986 2$^{nd}$ edition) designations. Where dimensions, sizes, colors, and other characteristics are given, it is to be understood that such characteristics are approximations of averages set forth as accurately as practicable.

Plants used for botanical data were three years old and grown on a fine sandy loam soil with trickle irrigation near Clarksville, Ark. The plants were fertilized near budbreak (late March on average) with complete or nitrogen fertilizer, and had an additional nitrogen fertilizer application in early July. Primocanes were tipped at approximately 45 inches, and grown in a hedgerow training system. Weeds were controlled with pre- and post-emergence herbicides supplemented with mechanical weed control activities. A single application of liquid lime sulfur was applied to the plants at budbreak, but no other fungicides were used. The descriptions reported herein are from specimens grown near Clarksville, Ark. unless otherwise noted.

Plant:

*Size*.—Plants are grown in a hedgerow and primocanes tipped at approx. 45-55 inches; plants in this system then range in size from approx. 45-55 inches tall and 36-40 inches wide.

*Growth habit*.—Moderate vigor, canes erect; suckers from crown and roots.

*Growth rate*.—Primocanes 1$^{st}$ emergence is March 24 and primocanes reach tipping height (107 cm) on May 31.

*Productivity*.—Floricane: 4.4 kg (9.7 lb/plant), comparable to 'Natchez' (U.S. Plant Pat. No. 20,891). Cold hardiness: Hardy to 2° F. (−16.6° C.) comparable to 'Natchez'. The low temperature of 2° F. was the lowest the cultivar has been exposed to and fruited successfully after this exposure. Chilling requirement: Estimated to be 200-300 hours below 45° F. (7.2° C.), lower than that of 'Ouachita' (400-500 hours).

Canes: Thorny, erect.

*Floricane* (*dormant or winter cane*).—Cane diameter: Base 1.73 cm; midpoint 1.10 cm; terminal 0.71 cm. Internode length: Base 4.19 cm; midpoint 8.97 cm; terminal 5.39 cm. Floricane color: Base mostly Green Group (146C) with some Green-Red Group (178A); midpoint Green Group (146C) with some Green-Orange Group (166A); terminus Yellow-Green Group (146B) with some Green-Orange Group (176A). Thorn-density (per 30 cm of cane length): Base 39.8; midpoint 28.8; terminus 30.3. Thorn length (from tip of thorn to bottom of thorn base): 5.0 mm, with non-curved thorn. Thorn Width: base: 1.2 mm; middle: 0.62 mm; tip: 0.24 mm. Thorn Color: Base and middle: grayed purple group 183-C; tip: grayed orange group 174-C.

*Primocane* (*current-season cane*).—Cane diameter: Base 1.85 cm; midpoint 1.01 cm; terminal 0.48 cm. Internode length: Base 6.58 cm; midpoint 4.72 cm; terminal 7.19 cm. Primocane color: Base Yellow-Green Group (145A) with some Red-Purple Group (60A); midpoint Yellow-Green Group (145A) with some Red-Purple Group (60A); terminus Green Group (143C) and Red-Purple Group (60A). Thorn density (per 30 cm of cane length): Base 35.5; midpoint 47.5; terminus 30.5. Thorn length (from tip of thorn to bottom of thorn base): 4.5 mm, with non-curved thorns. Date of primocane emergence: May 24. Disease resistance: Moderate resistant to anthracnose, and plants susceptible to orange rust. No screening has been done for resistance to double blossom/rosette.

Foliage:

*Primocane*.—Leaves: Large; mature compound leaf width 29.09 cm; length 17.65 cm. Leaflet: Width 9.78 cm; length 13.16 cm; shape round with acuminate apex and rounded very slightly cordate base; margin doubly serrated, serration teeth length 0.21 cm and width 0.22 cm; pubescence is very light on abaxial and adaxial surfaces; number of leaflets per compound leaf 5. Color: Base abaxial Green Group (137C); adaxial Green Group (135B); midpoint abaxial Green Group (138A); adaxial Green Group (132B); terminal abaxial Yellow-Green Group (147B); adaxial Green Group (137A). Petioles: Length: 7.41 cm; color: Red-Purple Group (60A) over Yellow-Green Group (144A); texture smooth. Petiolules: Length: 1.83 cm; color: Red-Purple Group (60A) over Yellow-Green Group (144A); texture smooth. Stipules: Length: 1.15 cm; width: 0.09 cm; texture smooth.

*Floricane*.—Leaves: Large; mature compound leaf width 20.82 cm; length 15.36 cm. Leaflet: Width 6.43 cm; length 8.13 cm; shape ovate to round with acuminate apex and rounded base; margin doubly serrated, with serration teeth length 0.27 cm and width at base 0.34 cm; pubescence is present moderately on the abaxial side very lightly on the adaxial side. Number of leaflets per compound leaf ranges from 3 to 5. Color: Base abaxial Green Group (138A); adaxial Green Group (137A); midpoint abaxial Green Group (137C); adaxial Green Group (137A); terminal abaxial Green Group (137B); adaxial Green Group (137A). Petioles: Length 4.52 cm; color: Green Group (143A); texture smooth. Petiolules: Length 1.17 cm; color: Yellow-Green Group (144A); texture smooth. Stipules: Length 0.83 cm; width: 0.14 cm: texture: smooth.

Flowers:

*Floricane*.—Date of bloom: 10% bloom March 31; 50% bloom April 8; last bloom April 12. Petal color: White Group (155D) with Purple Group (75D) blush. Reproductive organs: Stamens — erect, numerous. Pistils — numerous. Pollen — normal, fertile, and abundant. Flower diameter: 3.62 cm. Petal size: Length 2.12 cm; width 1.71 cm. Average number flowers per cluster: 5 to 6. Average number of petals per flower: 5. Number of sepals per flower: 5. Peduncle length: 1.18 cm. Peduncle color: Yellow-Green Group (144A). Cyme type: Elongate simple dichasium cyme. Cyme (flower cluster) length: ave 151.1 mm.

Fruit:

*Floricane*.—Maturity: Average first ripe date June 9, 3 days after 'Natchez'; with a fruiting period of 30-35 days. Size: Large, average 7-10 g. Diameter of fruit at primary position on inflorescence: Equator 2.28 cm; base pole 1.77 cm; terminal pole 1.15 cm. Diameter of fruit at secondary positions on inflorescence: Equator 1.97 cm; base pole 1.54 cm; terminal pole 1.04 cm. Length (primary fruit): 3.56 cm. Shape: Elongated conical to blocky. Color: Black Group (202A). Drupelet size: 0.52 cm. Seed (drupe): average length 4.0 mm; width 2.3 mm; dry weight (50 seed weight) 0.2 g; dry color Greyed-Orange (164B). Soluble solids: 11.9%. pH: 2.77. Acidity: 0.68 g/100 ml expressed as citric acid. Processed quality: Not evaluated for processing. Uses: Fresh market use for shipping is the primary market due to excellent postharvest handling capability, but can also be used for other fresh market use including local sales.

The cultivar: The most distinctive features of the cultivar are firm, large, sweet fruit with excellent postharvest handling potential, attractive fruit appearance, very good flavor, excellent plant health, potential reduced chilling requirement compared to other cultivars, and high yields.

I claim:

1. A new and distinct cultivar of blackberry plant named 'A-2312', substantially as illustrated and described.

* * * * *